(12) United States Patent
Weber et al.

(10) Patent No.: US 12,138,190 B1
(45) Date of Patent: Nov. 12, 2024

(54) UNIVERSAL HAND BRACE (71) Applicant: WEBER ORTHOPEDIC, L.P., Santa Paula, CA (US)

(72) Inventors: James J. Weber, Santa Barbara, CA (US); James Buckhout, Keller, TX (US); Jamie McMillan, Glendive, MT (US); Janakiram Srinivasa Rao Chetlapalli, Frisco, TX (US)

(73) Assignee: Weber Orthopedic, L.P., Santa Paula, CA (US)

( * ) Notice: Subject to any disclaimer, the term of this patent is extended or adjusted under 35 U.S.C. 154(b) by 0 days.

(21) Appl. No.: 18/434,257

(22) Filed: Feb. 6, 2024

Related U.S. Application Data

(60) Provisional application No. 63/443,689, filed on Feb. 6, 2023.

(51) Int. Cl.
*A61F 5/01* (2006.01)

(52) U.S. Cl.
CPC .................................. *A61F 5/0118* (2013.01)

(58) Field of Classification Search
CPC .. A61F 5/0118; A61F 13/108; A61F 5/05841; A61F 5/0585; A61F 5/05858; A61F 5/05866; A61F 5/05875; A61F 5/37; A41D 13/08; A41D 13/081; A41D 13/087; A41D 13/088
USPC .................................................. 128/878–882
See application file for complete search history.

(56) References Cited

U.S. PATENT DOCUMENTS

| | | | | |
|---|---|---|---|---|
| 2,095,603 | A * | 10/1937 | Langdon | A61F 5/05875 |
| | | | | D29/113 |
| 5,676,642 | A * | 10/1997 | Peters | A61F 5/34 |
| | | | | 602/23 |
| 7,276,039 | B2 | 10/2007 | Garelick et al. | |
| 7,278,980 | B1 | 10/2007 | Garelick et al. | |
| 7,402,149 | B1 | 7/2008 | Garelick et al. | |
| 7,442,177 | B1 | 10/2008 | Garelick et al. | |
| 7,455,650 | B1 * | 11/2008 | Garelick | A61F 5/0118 |
| | | | | 602/5 |
| 9,782,285 | B1 * | 10/2017 | Weber | A61F 5/0118 |
| 2006/0264792 | A1 | 11/2006 | Bonn | |
| 2020/0008967 | A1 * | 1/2020 | Hadjebi | A61F 7/02 |

* cited by examiner

*Primary Examiner* — Keri J Nelson
*Assistant Examiner* — Seth R. Brown
(74) *Attorney, Agent, or Firm* — Paul Y. Feng; One LLP (57) ABSTRACT

A finger and hand brace includes an elongated brace body applied lengthwise to the wrist and finger regions of the hand, with multiple straps extending from the brace body. The straps have sufficient length to wrap about at least two of the hand, wrist, a finger or fingers. Hook-and-loop fasteners on the brace body retain the straps in a wrapped condition. At least two elongated stiffeners are carried by the brace body inside pockets. A separation line, located at about the wrist, extends laterally across the brace body and enables the brace body to be separated into a distal/finger portion discrete from a proximal/wrist portion. The stiffeners and pockets are likewise separable into distal and proximal portions. The distal portion of the brace body includes a flap that holds the distal portion to the proximal portion of the brace body.

19 Claims, 10 Drawing Sheets

UNIVERSAL HAND BRACE

CROSS-REFERENCE TO RELATED APPLICATIONS

This application claims priority to provisional patent application No. 63/443,689, filed Feb. 6, 2023, the entire contents of which are incorporated by reference.

FIELD OF THE INVENTION

The present invention relates to an orthopedic brace. More particularly, the present invention relates to an improved hand brace.

BACKGROUND

There are over 1,500,000 metacarpal and phalangeal fractures each year. A large percentage of these involve a fracture of the fourth or fifth metacarpal shaft and neck. This injury is commonly known as a "boxer's fracture," as it is often the result of someone striking or punching an object harder than the hand, such as a wall or another person's head during a boxing match. The traditional treatment for such an injury is three to six weeks of cast immobilization. Due to how these types of injuries occur, they are often experienced in younger, more active individuals. In such patients, there is a high desire and need to return to work and/or physical and athletic activities as quickly as possible. Therefore, there exists a need for treatment of these types of injuries in such a way as to allow an accelerated return to normal activities by the patient in an easy and hand flexible manner.

SUMMARY OF THE INVENTION

The present invention in a preferred embodiment is directed to a finger and hand brace that wraps at least two of a wearer's hand, wrist, finger or fingers. The brace comprises an elongated brace body, adapted to be applied lengthwise to the wrist and finger regions of the hand, a plurality of flexible straps spaced apart lengthwise and extending from the brace body, wherein the straps are configured to wrap about at least two of the hand, the wrist, and at least one finger of the wearer. The brace includes retention means, preferably hook-and-loop fasteners or the like, disposed on the brace body to retain the straps in a wrapped condition.

The brace further includes a plurality of elongated stiffeners carried in pockets by the brace body, wherein at least one stiffener includes an undulating extent having at least one of a convex and concave curvature to conform to wrist and finger contours with the finger extended in natural condition, and wherein the at least one stiffener is formed from discrete first and second pieces that are detachably joined together at an interface. The interface is preferably a sleeve that frictionally holds the first and second pieces together, and allows the two pieces to be pulled apart when necessary.

The brace body optionally has an intermediate extent located between the pockets and stiffeners, and when folded, the straps wrap about the folded intermediate extent and about at least one of the pockets to exert positive retention compression on the pockets and stiffeners. The brace body further includes a separation line formed laterally across the brace body proximate to the wearer's wrist to enable the brace body to be separated into a distal or finger portion and a proximal or wrist portion, wherein the proximal portion including the second piece of the stiffener are detachable from the brace body.

The brace body has a plurality of pockets that longitudinally extend across the separation line and that receive the stiffeners therein, wherein the pockets have a proximate portion separable from a distal portion coinciding with the separation line, and wherein the distal pocket portion carries the first piece of the stiffener therein and the proximal pocket portion carries the second piece of the stiffener therein.

A flap is located at the separation line of each distal pocket portion that selectively attaches to and detaches from each of the proximal pocket portion, and when detached from the proximal pocket portion, folds to close the distal pocket portion enclosing the stiffener piece therein.

The finger and hand brace in exemplary embodiments has straps of sufficient length to wrap about one or more fingers as well as the hand. As such, a strap of the present invention brace can wrap around the fourth and fifth metacarpals to function as a "boxer splint." The strap can wrap around the third and fourth metacarpals to function as a "buddy splint." Or the strap can wrap around the second and third metacarpals to function as a radial gutter splint.

After sufficient recovery of the hand injury, the proximal portion of the brace body including the second stiffener piece can be detached and discarded to allow free movement of the wrist. The "cut down" distal portion of the brace body and stiffener can continue to be used on the patient's hand until full recovery is achieved.

Finally, the brace body is preferable symmetrical along a longitudinal centerline to enable the same brace to be applied to either the left hand or the right hand. This saves on the inventory carried by the clinic or hospital as compared to a dedicated left-hand-only or right-hand-only brace.

DETAILED DESCRIPTION OF THE PREFERRED EMBODIMENTS

The present invention relates to a novel hand immobilizing orthopedic brace that is useful for a large group of patients based upon its ease of application to the hand, and its moldability to the hand, its flexibility, reversibility, and improved healing promotion capabilities. Further, the present invention hand brace enables a patient to quickly return to normal work and/or physical activities. The versatile, moldable brace is typically configured to immobilize the fourth and fifth metacarpal fractures as well as phalangeal fractures, while at the same time being easily removable from the patient. Therefore, the brace is readily conformable or moldable to easily fit a large number of patients' hands through the use of semi-rigid inserts or stiffeners received in elongated pockets in an elongated brace body. The inserts, stays, or stiffeners are positioned to enable reversibility of the brace for use on a fracture of either hand.

Figure 1:
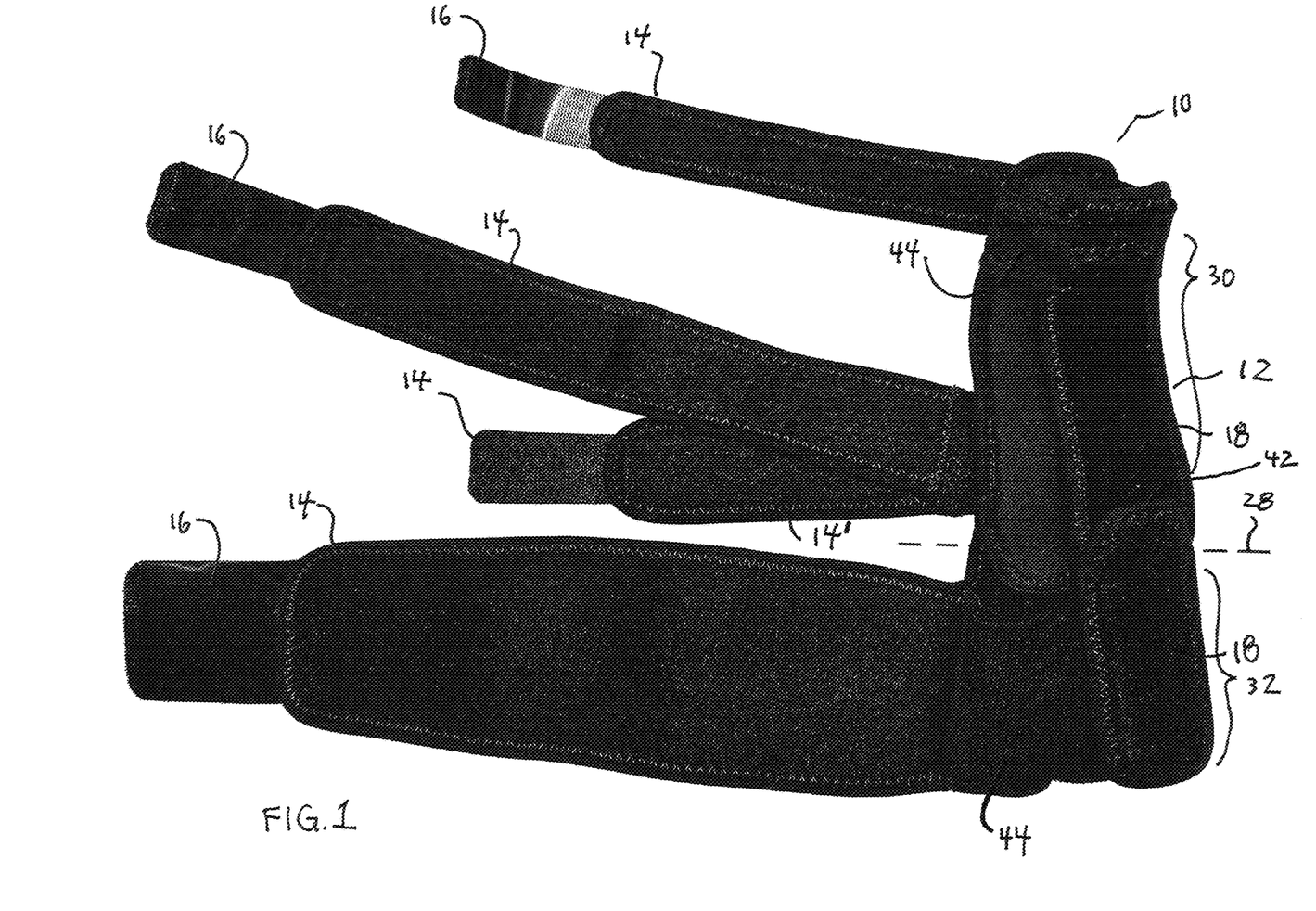
FIG. 1 is a side view of a preferred embodiment finger and hand brace.
Figure 2:
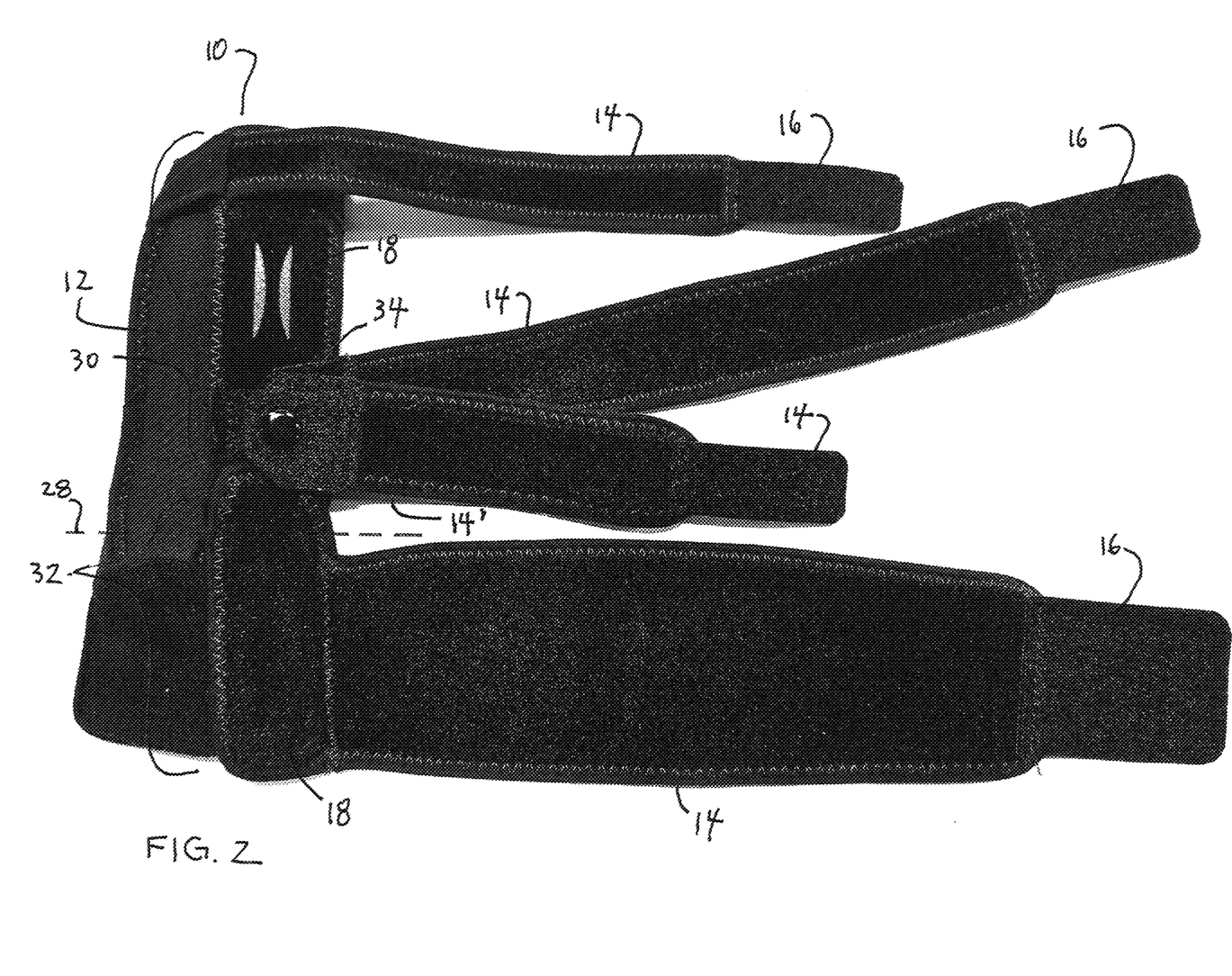
FIG. 2 is an opposite side view of the finger and hand brace of FIG. 1.

In a preferred embodiment depicted in FIGS. 1 and 2, the finger and hand brace 10 includes: (a) a longitudinally elongated brace body 12, which is preferably a pliable sheet, adapted to be wrapped lengthwise around the wrist and finger regions of the hand; (b) multiple flexible straps 14 carried by the body 12 to be spaced lengthwise thereof and to extend from the body; (c) separate straps 14 configured to be securely wrapped about at least two of the hand, the wrist, a finger or fingers; (d) retention means, e.g., hook-and-loop fasteners 16, positioned on the straps 14 attach and hold the straps in wrapped condition to the brace body's external fabric; (e) one or more generally elongated stiffeners 24, 26 (FIGS. 8, 10, 11) carried by the pockets 18 on the brace body 12, wherein the stiffeners having undulating extent or section, to readily conform to the wrist and finger contours with the fingers extended in natural condition; such stiffener undulating extents (FIGS. 8, 10, 11) may include a concave curvature, defined for example, by one stiffener to conform to palm curvature, or the convex curvature, defined by a second stiffener, to conform to knuckle curvature; (f) the brace body 12 includes a separation line 28 comprised of, for example, perforations, a cut line, thinned fabric line, or the like so the proximal wrist portion may be separated from the finger/palmar/distal portion, thereby freeing up movement for the patient's wrist as he or she undergoes recovery; and (g) one or more of the elongated stiffeners or stays 24, 26 (FIGS. 8, 10, 11) may be separated into two shorter components, such that when the wrist/proximal portion of the body is separated, the exposed length of the stiffener can likewise be detached from the portion of the stiffener that remains inside the finger/distal portion of the brace body 12.

Pockets 18 formed in the brace body 12 receive the stiffeners 24, 26 therein. Preferably, two of the straps wrap about both pockets with stiffeners therein. The brace body holds the undulating stiffeners proximate the palm and knuckle, respectively, in a wrapped condition of the brace, as shown in FIGS. 12, 13, 15-17.

Figure 14:
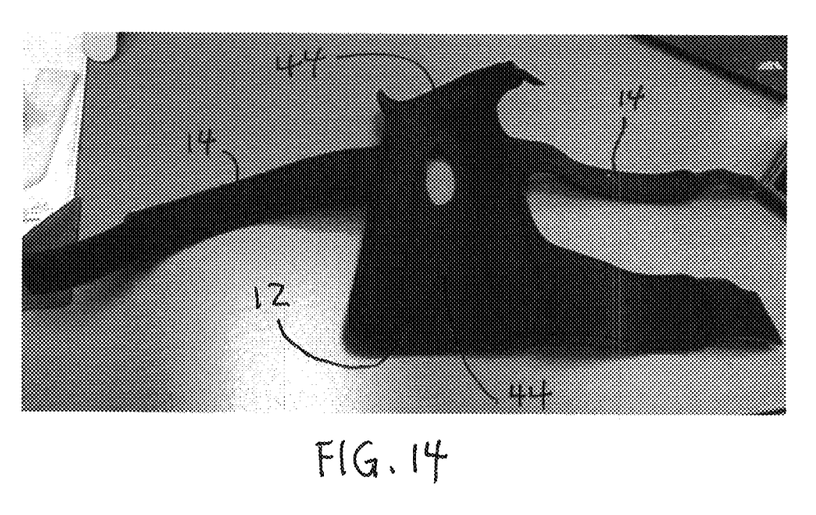
FIG. 14 shows an alternative embodiment finger and hand brace laid open.

In one embodiment shown in FIG. 14, the brace body 12 may have an extended position lying in a substantially flat plane, in which a body intermediate extent 44 is located between the pockets, the brace body merging with the straps 14 at a side of one pocket opposite the intermediate extent 44, the intermediate extent extending lengthwise throughout the major length of the pockets. As best seen in FIG. 14, the brace body 12 is generally symmetrical along a centerline, so the brace may be applied to either the left hand or the right hand. Further, the brace may be reversable so that it can be worn inside out, for example. The intermediate extents 44 of the brace body 12 can be seen in the FIG. 1 embodiment too. The brace body 12 in the FIG. 1 embodiment is also generally symmetrical along a longitudinal centerline so that it may be applied to either of the patient's left or right hand.

In various alternative embodiments, the present invention further includes a finger, hand, wrist brace with a volar/palmer stay and a dorsal stay that break down to a finger and hand brace comprising the following alternative configurations to fit the finger, hand, and wrist:

A. Finger, Hand and Wrist Combination of Metacarpal 4 and Metacarpal 5 of the Right Hand and Proximal Phalange or Phalanges 4 and Proximal Phalange or Phalanges 5 Right Hand.

B. Finger, Hand and Wrist Combination of Metacarpal 3 and Metacarpal 4 of the Right Hand and Proximal Phalange or Phalanges 3 and Proximal Phalange or Phalanges 4 Right Hand.

C. Finger, Hand and Wrist Combination of Metacarpal 2 and Metacarpal 3 of the Right Hand and Proximal Phalange or Phalanges 2 and Proximal Phalange or Phalanges 3 Right Hand.

D. Finger, Hand and Wrist Combination of Metacarpal 4 and Metacarpal 5 of the Left Hand and Proximal Phalange or Phalanges 4 and Proximal Phalange or Phalanges 5 Left Hand.

E. Finger, Hand and Wrist Combination of Metacarpal 3 and Metacarpal 4 of the Left Hand and Proximal Phalange or Phalanges 3 and Proximal Phalange or Phalanges 4 Left Hand.

F. Finger, Hand and Wrist Combination of Metacarpal 2 and Metacarpal 3 of the Left Hand and Proximal Phalange or Phalanges 2 and Proximal Phalange or Phalanges 3 Left Hand.

Still further alternative embodiments of the present invention include a finger, hand and wrist brace with a volar/palmer and dorsal stays that break down to a finger and hand brace comprising the following alternative configurations to fit the finger and hand:

G. Finger and Hand Brace Combination of Metacarpal 4 and Metacarpal 5 of the Right Hand and Proximal Phalange or Phalanges 4 and Proximal Phalange or Phalanges 5 Right Hand.

H. Finger and Hand Brace Combination of Metacarpal 3 and Metacarpal 4 of the Right Hand and Proximal phalange or Phalanges 3 and Proximal Phalange or Phalanges 4 Right Hand.

I. Finger and Hand Brace Combination of Metacarpal 2 and Metacarpal 3 of the Right Hand and Proximal Phalange or Phalanges 2 and Proximal Phalange or Phalanges 3 Right Hand.
J. Finger and Hand Brace Combination of Metacarpal 4 and Metacarpal 5 of the Left Hand and Proximal Phalange or Phalanges 4 and Proximal Phalange or Phalanges 5 Left Hand.
K. Finger and Hand Brace Combination of Metacarpal 3 and Metacarpal 4 of the Left Hand and Proximal Phalange or Phalanges 3 and Proximal Phalange or Phalanges 4 Left Hand.
L. Finger and Hand Brace Combination of Metacarpal 2 and Metacarpal 3 of the Left Hand and Proximal Phalange or Phalanges 2 and Proximal Phalange or Phalanges 3 Left Hand.

Figure 12:
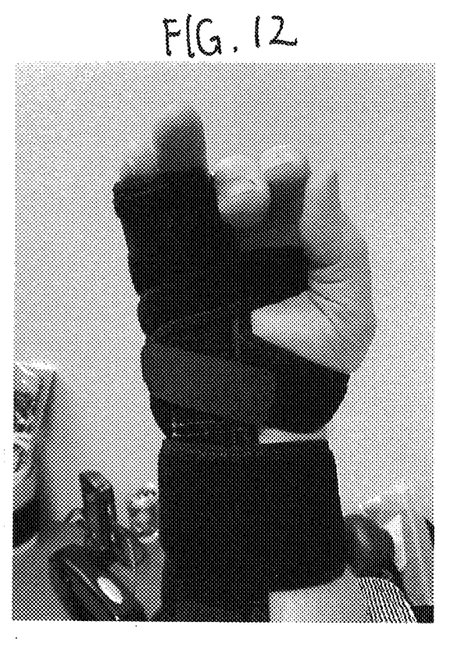
FIG. 12 shows the finger and hand brace applied to a patient's hand with the distal and proximal body portions joined together.
Figure 13:
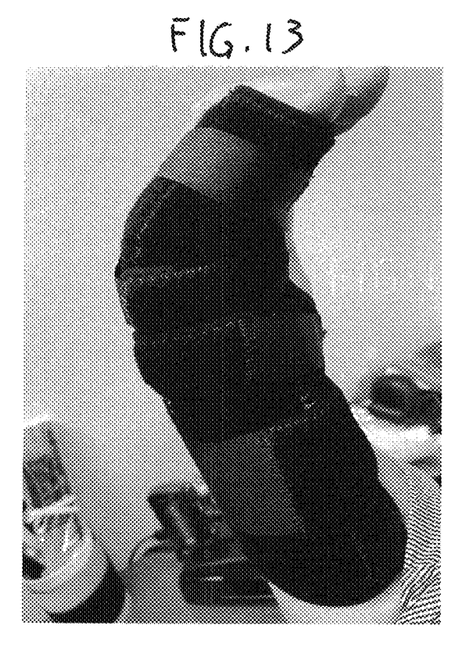
FIG. 13 is another view of the finger and hand brace of FIG. 12 applied to a patient's hand with the distal and proximal body portions joined together.
Figure 15:
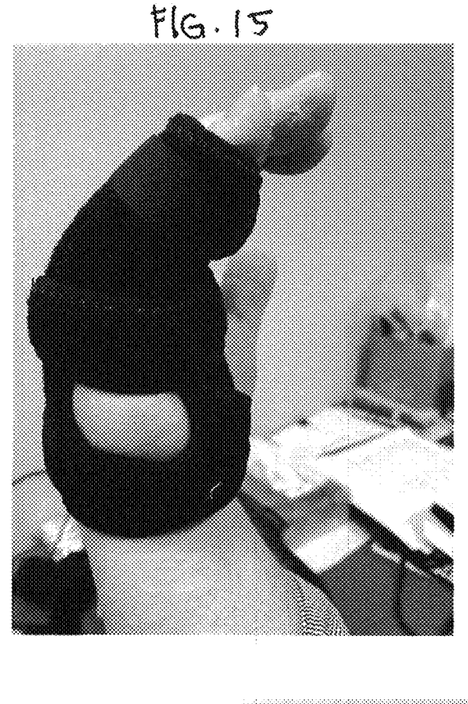
FIG. 15 shows the finger and hand brace applied to a patient's hand with the proximal portion detached and removed.
Figure 16:
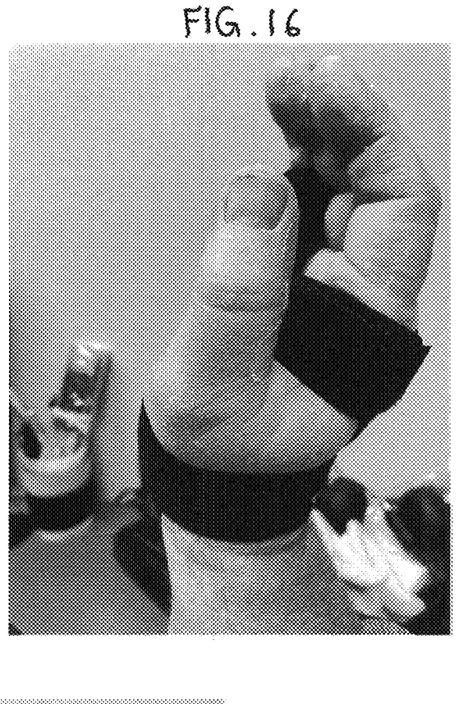
FIG. 16 is another view of the finger and hand brace of FIG. 15 applied to a patient's hand with the proximal portion detached and removed.
Figure 17:
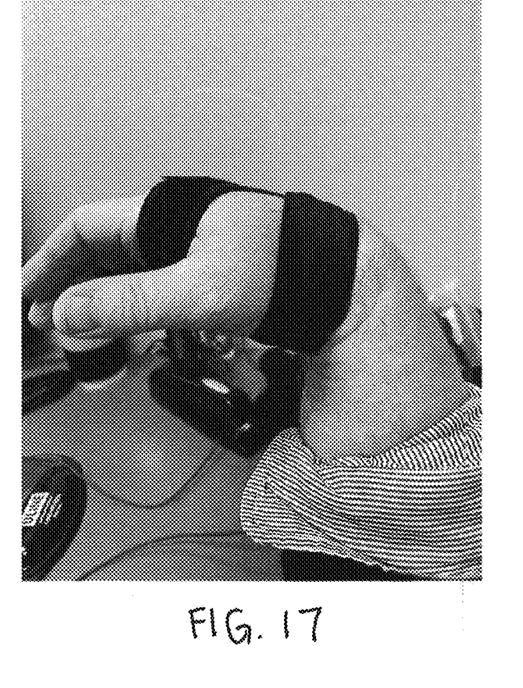
FIG. 17 is still another view of the finger and hand brace of FIG. 15 applied to a patient's hand with the proximal portion detached and removed.

As summarized above, the present invention preferred embodiments contemplate "total universality," meaning no need for a left- and a right-hand-dedicated versions, but just one that fits both the left and right hands with any combination of associated fingers on each hand. Moreover, the present invention hand brace breaks down from a Wrist-Hand-Finger Orthosis (WHFO) 20 as seen in FIGS. 12-13 to a hand-based Hand-Finger Orthosis (HFO) 22 as seen in FIG. 15-17. Thus, the present invention benefits from the ability to transform from a WHFO 20 to a HFO 22 as the patient heals, providing a continuum of care from initial fracture to healing.

After a certain point in care, usually a couple of weeks when the bone has begun to knit together, the present invention hand brace can be converted from a WHFO 20 to an HFO 22 by cutting or pulling apart the body and volar stay(s) into two discrete pieces. There is a separation line 28 or cut line, scoring line, perforation line, or the like for the physician, physical therapist, etc. to make the cut, pull apart, or tear and to separate the distal portion from the proximal portion of the brace body 12.

The lower portion contains the remnants of both the volar and the dorsal stays, while the upper portion has been completely separated now and transformed into a HFO. The stays are made of a fairly rigid metal such as aluminum or steel. They are made from two pieces that are fitted together, but may be manually separated back into two pieces. One piece is left inside the HFO while the other piece is no longer needed.

Once transformed into an HFO, the wrist moves freely, but the hand and specifically the metacarpals are still well supported. The current trend in orthopedic brace design is "less is more." Thus, the present invention brace can be easily converted to two applications. That is, as a hand-based splint is slowly becoming more acceptable in the industry, the present invention provides a WHFO and a HFO all in one brace. Furthermore, the WHFO and converted HFO can be applied to either left or right hand, and multiple fingers on either hand. This is the universal aspect of the present invention.

FIGS. 1 and 2 show a preferred embodiment finger and hand brace 10 having a longitudinal brace body 12 with a separation line 28 dividing the distal portion 30 from the proximal portion 32 of the brace body 12. A plurality of straps 14 extend from the brace body. Each strap 14 preferably has a retention means 16—preferably hook-and-loop fasteners (e.g., VELCRO®), hooks and receiving eyelets, D-rings with laces, clamps, or the like—at a distal end of the strap 14 to anchor against the brace body exterior. Preferably, the intermediate strap 14' nearest the separation line 28 includes a pivot or hinge 34 to allow the intermediate strap 14' to freely swivel relative to the brace body 12. This allows the intermediate strap 14' to freely swing upward to reach areas around the thumb, index and middle fingers for a radial gutter splint, for example. The pivot 34 may be a rivet, hinge, or the like.

Figures 8, 9:
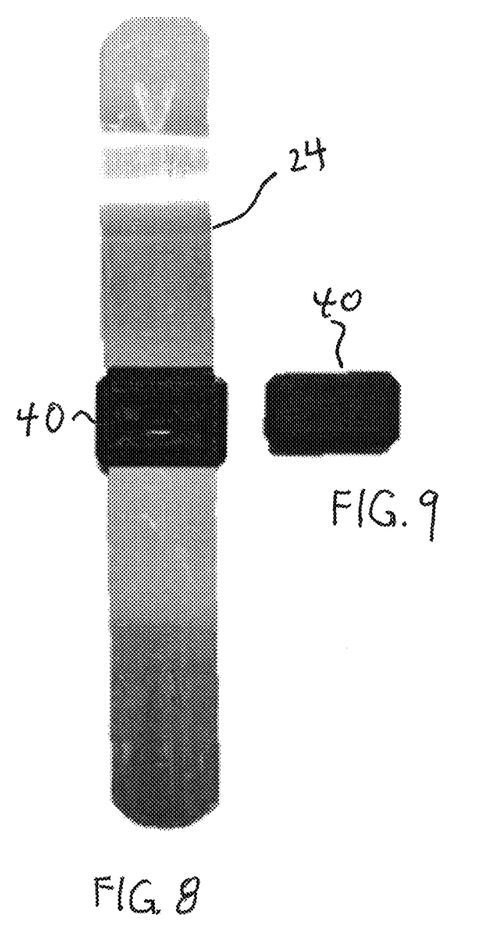
FIG. 8 shows a stiffener having a first piece joined to a second piece where the interface is a sleeve.
FIG. 9 is a view of the sleeve.
Figure 10:
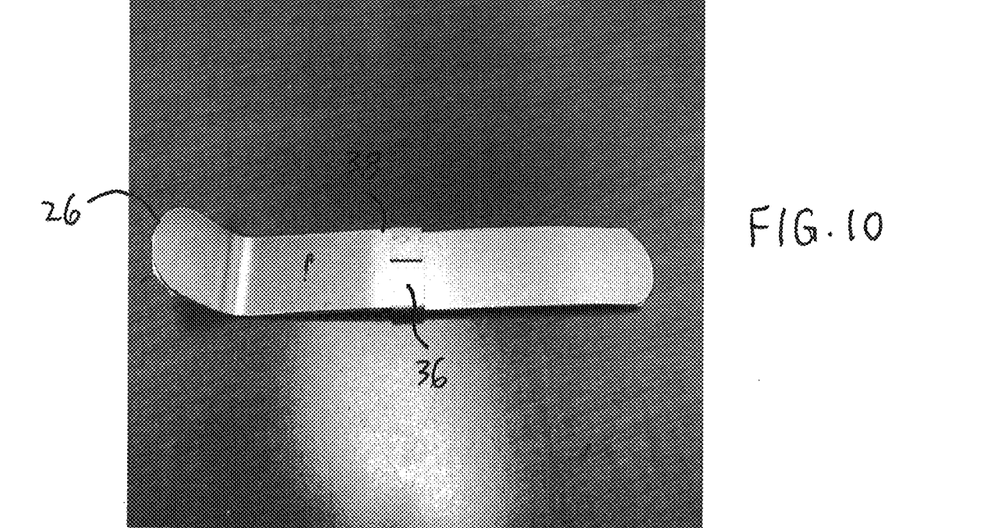
FIG. 10 shows an alternative embodiment stiffener having a first piece joined to a second piece wherein the interface is a tongue fitted inside a slot.
Figure 11:
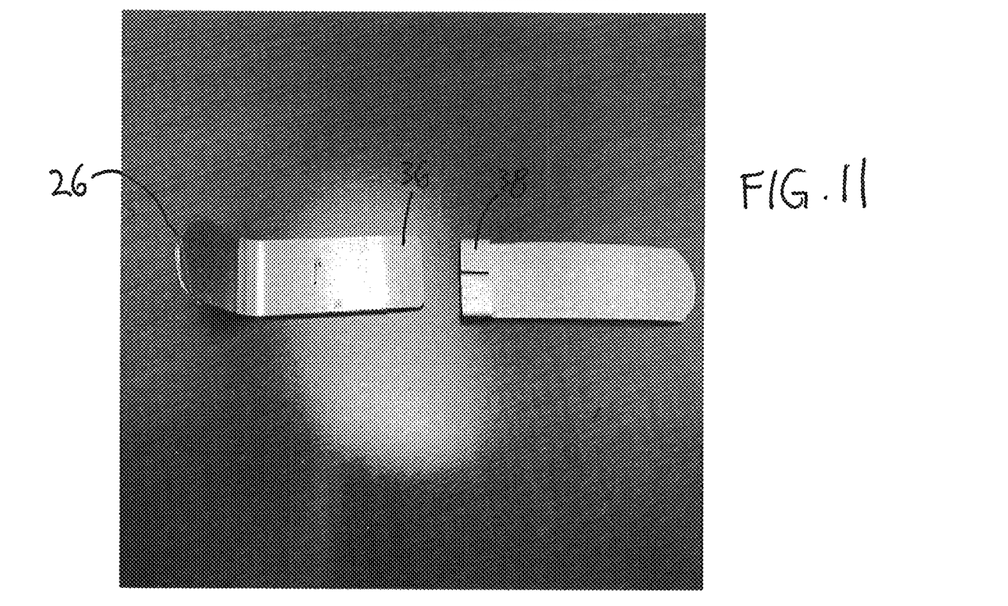
FIG. 11 shows the stiffener of FIG. 10 separated into its first piece and second piece.

As seen in FIG. 1, the brace body 12 has pockets 18 located on panels of the brace body interconnected by intermediate extents 44. The pockets 18 carry one or more stiffeners or stays 24, 26 therein. Each brace body panel with the pocket 18 and stiffener 24, 26 is positioned to overlie either the palmer/volar region or the dorsal region of the hand. As seen in FIGS. 8, 10-11, the stays or stiffeners 24, 26 preferably include undulating extents or sections with convex and concave curves to conform to the wearer's wrist and finger contours for improved comfort and support. The pockets 18 holding the stiffeners 24, 26 therein follow contours of the stiffeners, and that combination follows the contours of the hand in a relaxed state. The stiffeners 24, 26 may be fabricated from a malleable metal such as aluminum, so the contours may be bent to any desired shape.

Furthermore, the stiffeners 24, 26 in FIGS. 8, 10, 11, are made from, preferably, two discrete pieces. In the embodiment depicted in FIGS. 10, 11, the two pieces fit together at an interface via a tongue 36 engaging a slot 38. Alternatively, in the FIGS. 8, 9 embodiment, the two pieces of the stiffener 24 are held together at an interface by a sleeve 40. The sleeve 40 is made from a plastic or like material that may be sized or shrink-wrapped to tightly grip the two pieces. In both embodiments, friction or a temporary cement is used to hold the two pieces together, so when necessary, the two pieces can be pulled apart without much effort. This occurs when it is desired to separate the proximal/wrist portion 32 of the brace body from the distal/finger portion 30 of the brace, as explained above. The pockets 18 carrying the stiffeners 24, 26 therein are likewise separable into a distal portion and a proximal portion along the separation line 28.

Figure 3:
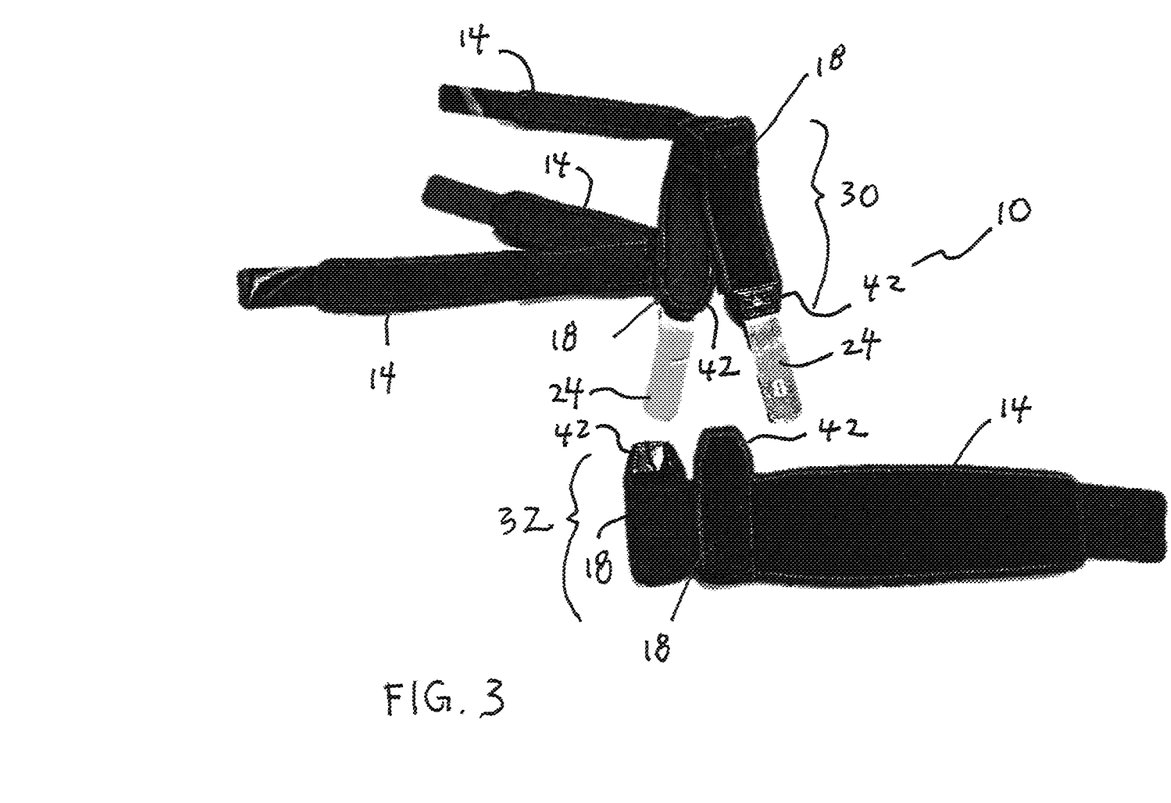
FIG. 3 shows the finger and hand brace of FIG. 1 separated into a distal/finger portion and a proximal/wrist portion.

FIG. 3 shows the preferred embodiment finger and hand brace 10 separated into a distal/finger portion 30 and a proximal/wrist portion 32. The strap 14 intended to wrap about the wearer's wrist has a broader width dimension for comfort, as compared to the other skinnier straps 14 that wrap about the wearer's fingers. The stiffeners 24 can be seen still inserted inside the pockets 18 at the distal portion 30 of the brace body, while the proximal length of the stiffeners is exposed. So in the FIG. 3 depiction, the proximal piece of the stiffener 24 has not yet been detached from the distal piece.

Also visible in FIG. 3 are trapezoidal-shaped flaps 42 that extend from the mouths or opening of the pockets 18. The flaps 42 have hook-and-loop fasteners that attach to the opposite portion of the brace body to hold the proximal and distal portions together. When separation is required for a "cut down" brace, the wearer can selectively flip up the flaps 42 to detached them from the surface of the opposite portion thereby releasing the attachment points. Now the proximal portion 32 and distal portion 30 of the brace body can be pulled apart. The proximal piece of the stiffener is then detached from the distal piece. Next, the flaps 42 flip down to close the mouth and enclose the distal piece of the stiffener captured within the distal pocket portion. This provides a finished, smooth edge at the separation line 28 without exposing the stiffener that may be unsightly and might abrade against the wearer's skin.

Figures 4, 5, 6, 7:
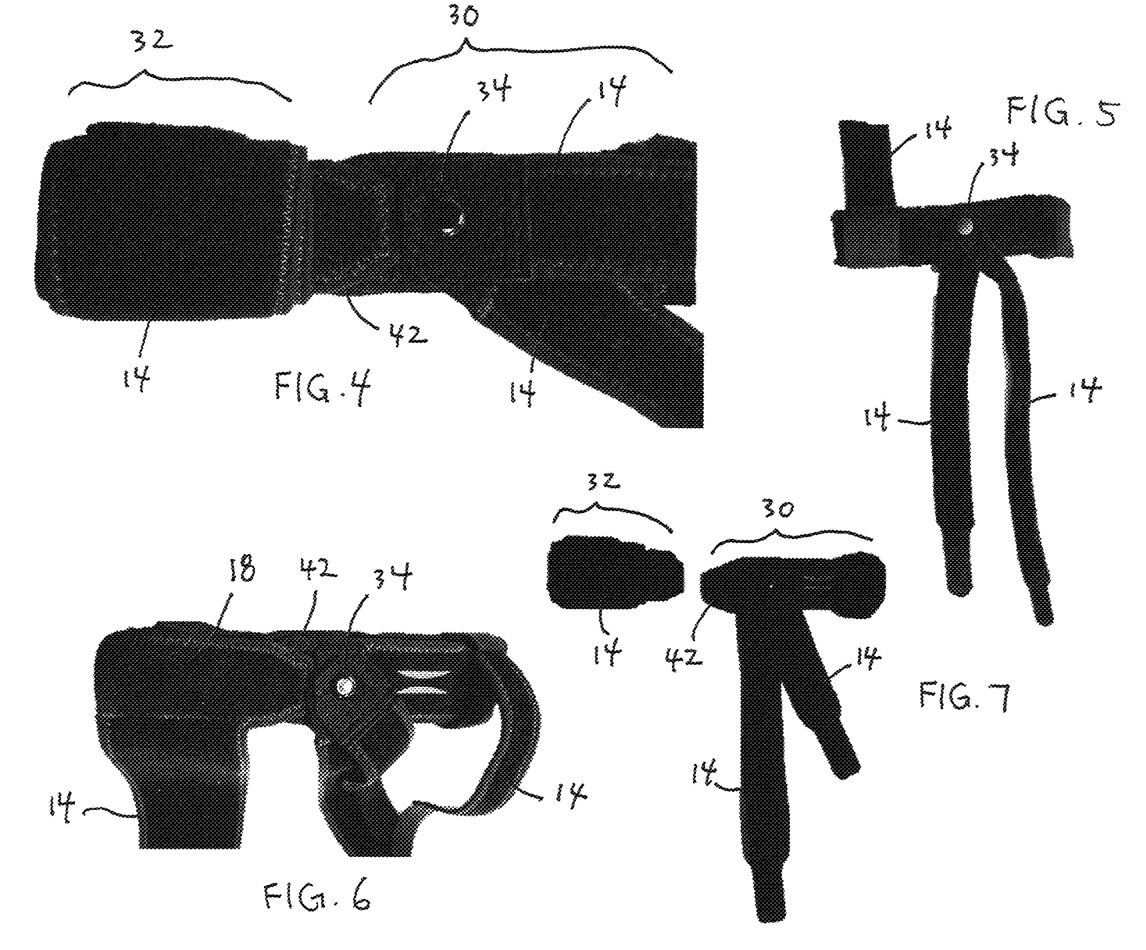
FIG. 4 is a magnified view of a strap pivotably attached to the brace body.
FIG. 5 is another view of a strap pivotably attached to the brace body with free strap ends.
FIG. 6 is another magnified view of the pivot attachment of the strap to the brace body.
FIG. 7 is a magnified view of the brace body separated into a distal portion and a proximal portion.

FIGS. 4, 5, and 6 are enlarged views of the preferred embodiment finger and hand brace 10, detailing the pivot location 34, strap arrangement, and the distal and proximal portions 30, 32 portions of the brace body being held together by the flap 42. FIG. 7 shows the proximal portion 32 separated from the distal portion 30 of the brace body with the flaps 42 in the flipped up, released position.

Figure 18:
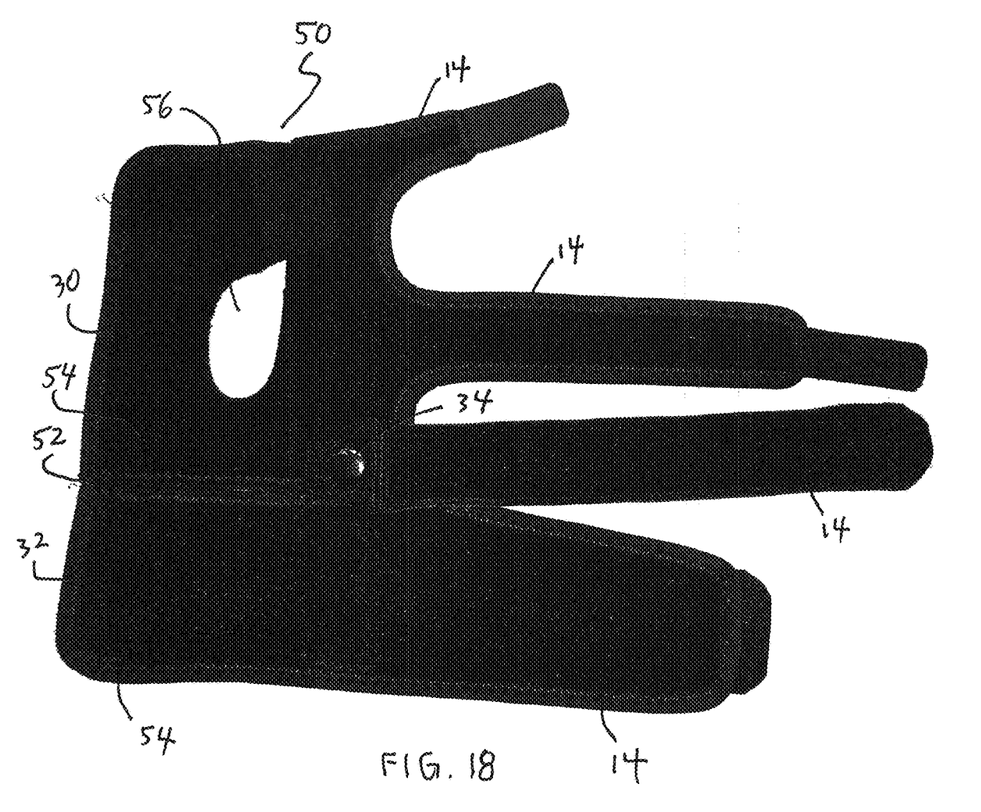
FIG. 18 is an alternative embodiment hand and finger brace with a cut guide formed at the separation line of the brace body to allow the distal portion to be cut and separated from the proximal portion.
Figure 19:
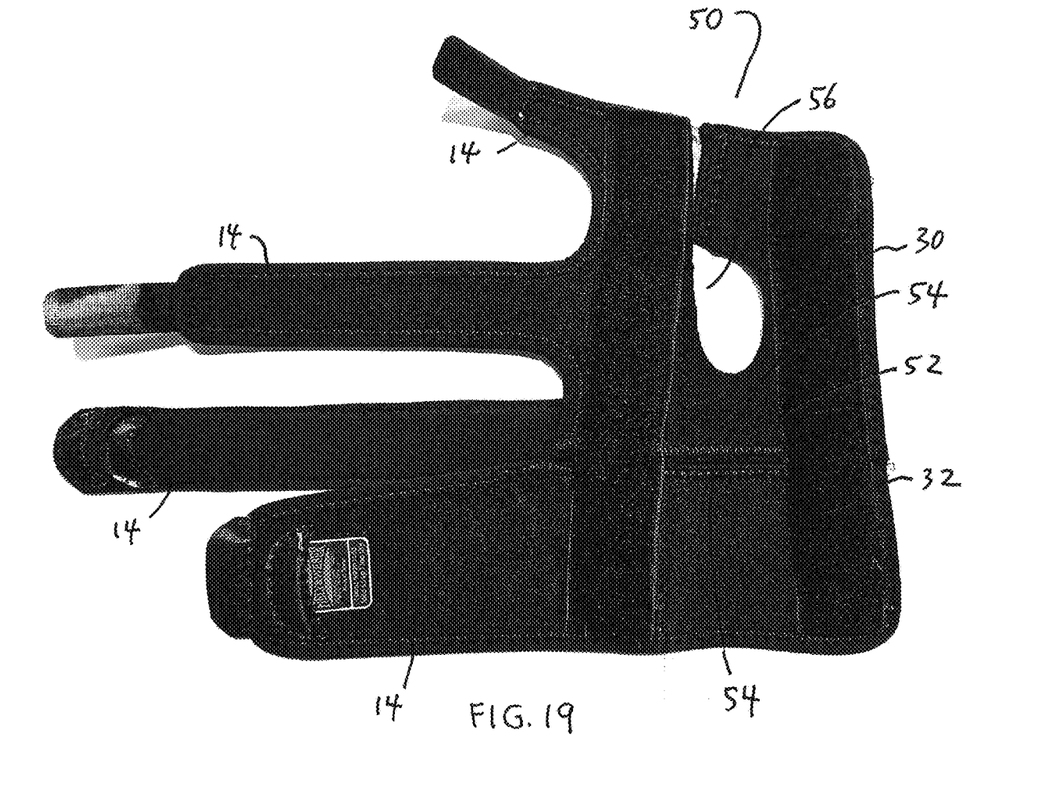
FIG. 19 is the back view of the alternative embodiment brace shown in FIG. 18.

FIGS. 18, 19 depict still another alternative embodiment of the present invention finger and hand brace 50. This is the "cut line" embodiment, which includes a cut line 52 of thinned fabric laid in between reinforced edges 54 dividing the distal portion 30 from the proximal portion 32 of the brace body. When there is a need to separate the two portions, the clinician, nurse, etc., cuts along the cut line with scissors or a scalpel, being guided therebetween by the reinforced edges 54. The stays or stiffeners carried inside the pockets can be separated into a distal piece and a proximal piece as described above with other embodiments. The pockets are made from soft fabric and can be cut along the cut line with the brace body. This embodiment may include an optional thumb opening 56 where the wearer's thumb may pass through when wearing this hand brace 50.

While particular forms of the invention have been illustrated and described, it will be apparent that various modifications can be made without departing from the spirit and scope of the invention. Furthermore, components from one embodiment may be modified or combined with the components from another embodiment.

What is claimed is:

1. A finger and hand brace that wraps at least two of a wearer's hand, wrist, finger or fingers, the brace comprising:
    an elongated brace body having a top interconnecting strip, an open center, and a bottom interconnecting strip, the body configured to be applied lengthwise to the wrist and finger regions of the left or right hand;
    a plurality of flexible straps spaced apart lengthwise and extending from the brace body, wherein the straps are configured to wrap about at least two of the hand, the wrist, and at least one finger of the wearer;
    retention means disposed on the brace body to retain the straps in a wrapped condition;
    a plurality of elongated stiffeners carried by the brace body, wherein at least one stiffener includes an undulating extent having at least one of a convex and concave curvature to conform to wrist and finger contours with the finger extended in natural condition, and wherein the at least one stiffener is formed from discrete first and second pieces that are detachably joined together at an interface, and wherein at least two of the stiffeners are configured to be overlying with each other and centered at the dorsal and palmer regions of the hand, and are joined only by the top and bottom interconnecting strips of the brace body;
    a separation line formed laterally across the brace body configured to be applied proximate to the wrist to enable the brace body to be separated into a distal portion and a proximal portion, wherein the proximal portion including the second piece of the stiffener is detachable from the brace, and wherein the separation line coincides with the open center of the brace body;
    a plurality of pockets disposed on the brace body that longitudinally extend across the separation line and that receive the stiffeners therein, wherein the pockets have a proximate portion separable from a distal portion along the separation line, and wherein the distal pocket portion carries the first piece of the stiffener therein and the proximal pocket portion carries the second piece of the stiffener therein;
    wherein the straps wrap about at least one of the pockets to exert positive retention compression on the pockets and stiffeners; and
    wherein the stiffener interface is located proximate to the separation line.

2. The finger and hand brace of claim 1, wherein the retention means includes a hook-and-loop fastener.

3. The finger and hand brace of claim 1, wherein the first and second discrete pieces of the stiffener are frictionally joined together by a sleeve.

4. The finger and hand brace of claim 1, wherein the first piece of the stiffener includes an end with a slot formed by bending arms inward to form the slot, and the second piece of the stiffener includes an end with a tongue that is inserted into the slot.

5. The finger and hand brace of claim 1, wherein at least one strap is pivotably attached to the brace body.

6. The finger and hand brace of claim 1, wherein at least one strap is hinged to the brace body with a rivet.

7. The finger and hand brace of claim 1, wherein the plurality of flexible straps includes at least three straps with two straps located in the distal portion of the brace body.

8. The finger and hand brace of claim 1, wherein at least one stiffener includes a malleable metallic material.

9. A finger and hand brace that wraps at least two of a wearer's hand, wrist, finger or fingers, the brace comprising:
    an elongated brace body having a top interconnecting strip, an open center, and a bottom interconnecting strip, adapted to be applied lengthwise to the wrist and fingers of the left or right hand;
    a plurality of flexible straps spaced apart lengthwise along the brace body and extending therefrom, wherein the straps are configured to wrap about at least two of the hand, the wrist, and at least one finger of the wearer;
    retention means disposed on the brace body to retain the straps in a wrapped condition;
    a plurality of elongated stiffeners carried on the brace body, wherein at least one stiffener includes an undulating extent having at least one of a convex and concave curvature to conform to wrist and finger contours, and wherein at least one stiffener is formed from discrete first and second pieces that are detachably joined together at an interface;
    a separation line formed laterally across the brace body coinciding with the open center of the brace body, and configured to be placed proximate to the wrist to enable the brace body to be separated into a distal portion and a proximal portion, wherein the proximal portion including the second discrete piece of the stiffener is detachable from the brace; and
    a plurality of pockets disposed on the brace body that longitudinally extend across the separation line and that receive the stiffeners therein, wherein the pockets carrying the stiffeners are configured to be centered at the dorsal and palmar regions of the hand and the stiffeners are aligned and overlying each other, and are joined by only the top and bottom interconnecting strips of the brace body, and wherein the pockets have a proximal portion separable from a distal portion coinciding with the separation line, and wherein the distal pocket portion carries the first piece of the stiffener therein and the proximal pocket portion carries the second piece of the stiffener therein.

10. The brace of claim 9, wherein the stiffener interface includes a plastic sleeve joining the first and second pieces of the stiffener.

11. The brace of claim 9, wherein at least one of the straps is hinged to the brace body with opposed free ends.

12. The brace of claim 9, wherein the straps include a hook-and-loop fastener that attaches to an exterior surface of the brace body.

13. A finger and hand brace that wraps at least two of a wearer's hand, wrist, finger or fingers, the brace comprising:
- an elongated brace body having a top interconnecting strip, an open center, and a bottom interconnecting strip that is configured to be applied lengthwise to the wrist and fingers of the left or right hand, the brace body having a panel configured to be proximate a dorsal region of the hand and a panel configured to be proximate a palmer region of the hand, and wherein the dorsal panel and palmar panel are joined only by the top and bottom interconnecting strips;
- a plurality of flexible straps spaced apart lengthwise along the brace body and extending therefrom, wherein the straps are configured to wrap about at least two of the hand, the wrist, and at least one finger of the wearer;
- retention means disposed on the brace body to retain the straps in a wrapped condition;
- a plurality of elongated stiffeners carried by the brace body at the dorsal panel and the palmer panel such that the stiffeners are configured to be centered at the dorsal and palmar regions and further aligned and overlying each other, wherein at least one of the plurality of stiffeners includes an undulating extent having at least one of a convex and concave curvature to conform to wrist and finger contours, and wherein the plurality of stiffeners are formed from discrete first and second pieces that are detachably held together at an interface;
- a separation line formed laterally across the brace body at the open center of the brace body and configured to be placed proximate to the wrist to enable the brace body to be separated into a distal portion and a proximal portion, wherein the proximal portion including the second piece of the stiffener is detachable from the brace body; and
- a plurality of pockets disposed on the brace body that longitudinally extend across the separation line and that receive the plurality of stiffeners therein, and wherein the pockets have a proximal portion separable from a distal portion coinciding with the separation line, and wherein the distal pocket portion carries the first piece of the stiffener therein and the proximal pocket portion carries the second piece of the stiffener therein.

14. The brace of claim 13, wherein the stiffener interface includes a plastic sleeve frictionally holding the first and second pieces of the stiffener together.

15. The brace of claim 13, wherein at least one of the straps is pivotably attached to the brace body with opposed free ends.

16. The brace of claim 13, wherein at least one strap is attached to the brace body to enable the strap to pivot relative to the brace body.

17. The brace of claim 13, wherein the retention means includes a hook-and-loop fastener.

18. The brace of claim 13, wherein the straps include sufficient length to wrap multiple fingers.

19. The brace of claim 13, wherein the brace body is symmetrical across a lengthwise centerline so that it is adapted for use on either the right hand or the left hand.

* * * * *